(12) United States Patent
Laghi et al.

(10) Patent No.: US 12,740,877 B2
(45) **Date of Patent: *Sep. 22, 2026**

(54) SOCKS AND LINERS WITH SHOCK ABSORBING PROPERTIES

(71) Applicant: Alps South, LLC, St. Petersburg, FL (US)

(72) Inventors: Aldo Laghi, Pinellas Park, FL (US); Jordan Wilkes, Thonotosassa, FL (US); David Carson, St. Petersburg, FL (US)

(73) Assignee: Alps South, LLC

( * ) Notice: Subject to any disclaimer, the term of this patent is extended or adjusted under 35 U.S.C. 154(b) by 518 days.

This patent is subject to a terminal disclaimer.

(21) Appl. No.: 18/376,149

(22) Filed: Oct. 3, 2023

(65) Prior Publication Data

US 2024/0024135 A1 Jan. 25, 2024

Related U.S. Application Data

(63) Continuation-in-part of application No. 18/373,099, filed on Sep. 26, 2023, which is a continuation of application No. 18/095,043, filed on Jan. 10, 2023.

(60) Provisional application No. 63/315,121, filed on Mar. 1, 2022.

(51) Int. Cl.
*A61F 2/78* (2006.01)
*A41B 11/00* (2006.01)

(52) U.S. Cl.
CPC .... *A61F 2/7812* (2013.01); *A61F 2002/7818* (2013.01)

(58) Field of Classification Search
CPC .. A61F 2/7812; A61F 2002/7818; A61F 2/78; A61F 2/50; A61F 2/00; A41B 11/005; A41B 11/02; A41B 11/00; A41B 11/007; A41B 11/008; A41B 11/121; A41B 13/08; A41B 13/06; A41B 13/00; D04B 1/26; D04B 1/24; D04B 1/22; D04B 1/00
See application file for complete search history.

(56) References Cited

FOREIGN PATENT DOCUMENTS

| | | | | | |
|---|---|---|---|---|---|
| CN | 110664023 | A | * | 1/2020 | A41B 17/00 |
| DE | 19544757 | A1 | * | 6/1997 | D04B 1/26 |
| GB | 728052 | A | * | 4/1955 | A41B 11/00 |
| GB | 2020958 | A | * | 11/1979 | A41B 11/00 |
| KR | 200440262 | Y1 | * | 6/2008 | A41B 11/02 |

* cited by examiner

*Primary Examiner* — Tarla R Patel
(74) *Attorney, Agent, or Firm* — Carlson IP Law, LLC

(57) ABSTRACT

A shock absorbing covering that has an opening, a closed liner distal end, and sidewalls. The distal end further comprises a distal region that is knitted with spacer fabric to the same circumference as the liner or sock or is configured to conform to specific areas of a foot; preferably, (1) the toe region leaving out the big toe region, (2) the metatarsal head (MTH) 1 region leaving out the MTHs 2-3 region and the MTHs 4-5 region, (3) the medial mid-foot region, (4) the lateral mid-foot region, and (5) the lateral heel region leaving out the medial heel region. The spacer fabric is preferred as a 2×2 knit outer wall with a 1×3 inner wall made using a number of knitting steps described herein but may be a multitude of configurations allowing for a continuous seamless shape in three dimensions. An alternative yarn may be used that is coated in poly(vinyl alcohol) that expands after being washed to create shock absorbing expansion pockets.

13 Claims, 25 Drawing Sheets

56
58
60
18

SOCKS AND LINERS WITH SHOCK ABSORBING PROPERTIES

CROSS-REFERENCE TO RELATED APPLICATIONS

This application is a continuation-in-part of application Ser. No. 18/095,043 titled "Socks and Liners with Shock Absorbing Properties" filed Jan. 10, 2023 which claimed the benefit of provisional application 63/315,121, filed Mar. 1, 2022, the disclosures of which are incorporated by reference herein.

BACKGROUND OF THE INVENTION

Field of the Invention

The described invention relates to socks and liners. Specifically, the described invention relates to socks and liners incorporating spacer fabrics utilizing specific yarns in specific knitting patterns which provide shock absorbing properties to the socks and liners.

Description of the Background Art

Ambulation for leg and foot amputees can be uncomfortable or even painful due to the ground response from the transmission of force shocks due to walking. Unlike the human foot or leg, a residual limb exhibits neither a tough or resilient skin structure nor a compliant skeletal structure, resulting in pain or discomfort for most amputees during ambulation. Even when a socket and interface are fit properly, amputees who engage in sports, amputees who are overweight, or amputees with bony prominences can feel discomfort or pain. Likewise, patients with nerve sensitivity due to neuropathy would benefit from a sock or liner with increased cushioning.

The ground response is transmitted to the skeleton of amputees by the socket through and interface which is either a knitted interface (i.e. a prosthetic sock) or a polymer interface (i.e. a prosthetic liner). Ideally, a prosthetic socket, when fit properly, should discharge ⅓ of an amputee's weight distally and ⅔ of an amputee's weight circumferentially. However, prosthetic socks and liners on the market currently do not provide features for attenuation of impact at the distal end during ambulation or other physical activity. Socks are presently in use that incorporate gel so as to attenuate impacts but these cannot be machine washed or dried.

Spacer fabrics contain a combination of textile sheets and distance fibers, with a porous structure that can offer high absorption capacities. Since the distance fibers are often monofilament fibers with a marked stiffness, spacer fabrics can resist pressure and have a directed transport of fluid and heat. The pressure-resistance property can also be adjusted by adjusting the type of fibers, the number of the fibers, the angle of the fibers in the textile structure, and the stitch density. Spacer fabrics are considered to be ideal for cushioning applications. Spacer fabrics are often warp knitted, have a face layer, a back layer, and an internal spacer layer. Spacer yarns are typically monofilaments that connect the two outer layers to form a three-dimensional structure. The number of fibers used can be adjusted so that the spacer yarns are multi-filament as well. Spacer fabrics are presently used in applications such as car seat padding for vibration reduction and breathable panels in apparel.

Because of the layer of these spacer yarns, a defined distance can be established between the outer layers, which generally varies from 1.5 mm to 10 mm. The design of construction affects the functionality of the 3D structure in terms of thermoregulation, breathability, pressure stability, and pressure elasticity. Both of the outer layers can be constructed with different materials or patterns. The material types and surface characteristics of the layers influence the elastic and comfort properties of the entire structure. The structure can be varied using different filaments for the outer layers (e.g. nylon, polyester, and cotton, among others) and the varying of the inner distance fibers of multiple monofilaments to adjust and control the rebound and energy absorption effects of the fabric layer.

Therefore, it is an object of this invention to provide an improvement which overcomes the aforementioned inadequacies of the prior art devices and provides an improvement which is a significant contribution to the advancement of the shock absorbing prosthetic liner art.

Another object of the invention is to provide a prosthetic sock or liner that decreases discomfort and pain during ambulation or athletics.

Another object of the invention is to provide a prosthetic sock liner that decreases discomfort and pain for overweight amputees.

Another object of the invention is to provide a sock or liner that can be used for diabetics or for individuals who stand for long periods of time.

Another object of the present invention is to provide a sock or liner that can be used for athletic activities and provides increased cushioning to decreased impact force.

Another object of the invention is to provide a sock that uses spacer material and is also machine-washable.

Another object of the invention is to provide a liner with a continuous gel or silicone interior that is augmented by spacer fabric creating a liner that is both shock absorbing and lighter weight.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The present invention relates generally to a shock absorbing covering that has an opening, a closed liner distal end, and sidewalls. The distal end further comprises a distal region that is knitted with spacer fabric to the same circumference as the liner or sock or is configured to conform to specific areas of a foot; specifically, (1) the toe region leaving out the big toe region, (2) the metatarsal head (MTH) 1 region leaving out the MTHs 2-3 region and the MTHs 4-5 region, (3) the medial mid-foot region, (4) the lateral mid-foot region, and (5) the lateral heel region leaving out the medial heel region. The spacer fabric is preferred as a 2×2 knit outer wall with a 1×3 inner wall made using a number of knitting steps described herein but may be a multitude of configurations allowing for a continuous shape in three dimensions. This structure allows three dimensional shapes to be formed and applied without stitching.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and its advantages, reference is now made to the following descriptions, taken in conjunction with the accompanying drawings, in which:

FIG. 11-1 is a blown-up view of the spacer fabric used in FIG. 6;

FIG. 12-1 is a blown-up view of the spacer fabric used in FIG. 7;

Similar reference numerals refer to similar parts throughout the several views of the drawings.

DETAILED DESCRIPTION OF THE PREFERRED EMBODIMENT

The following description is of the best mode presently contemplated for carrying out the invention. This description is not to be taken in a limiting sense, but is made merely for the purpose of describing one or more preferred embodiments of the invention. The scope of the invention should be determined with reference to the claims.

As can be seen in FIGS. 1-9, a force test was performed on a number of different substrates to demonstrate shock absorption capabilities. This test was performed on a structure with a 3.75-inch diameter striker weighing 16.5 pounds with a 3.1625 inch drop onto an anvil of 3.75 inches in diameter with a leather strike face of 2.5 inches in diameters and 0.185 inches in thickness.

Figure 1:
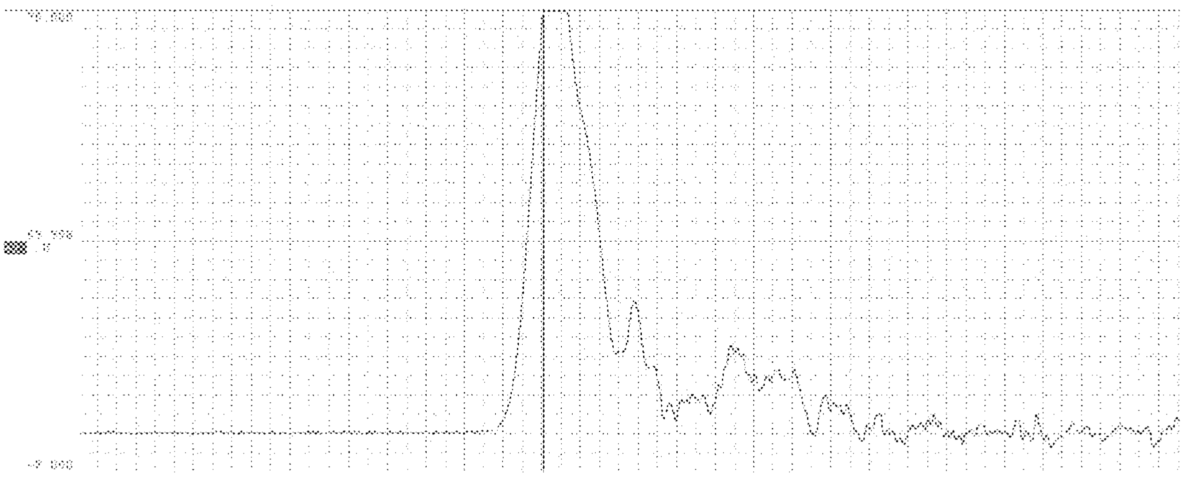
FIG. 1 is a graph showing the shock absorbing capabilities of a simple leather substrate.
Figure 2:
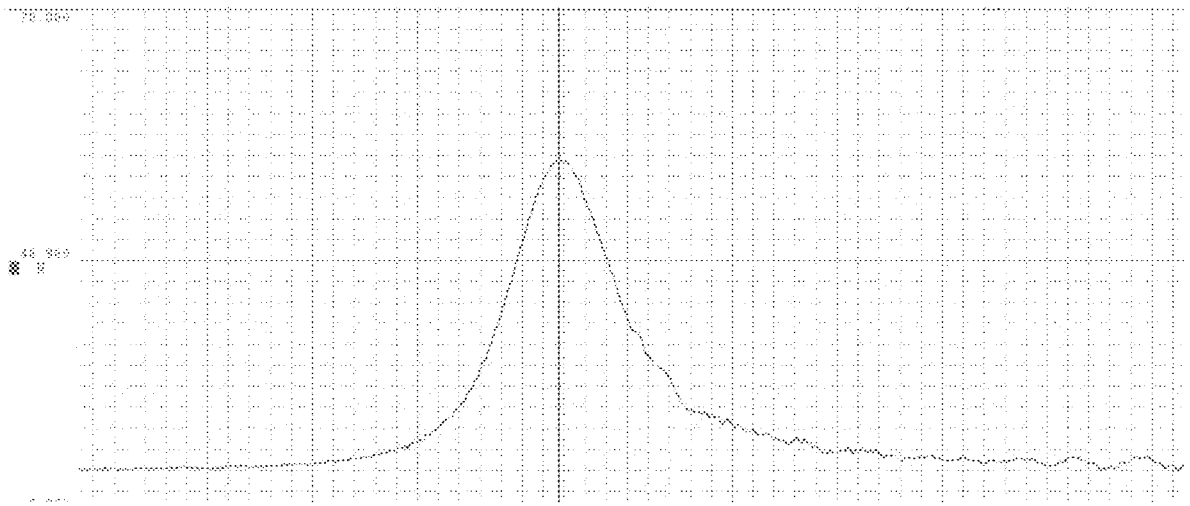
FIG. 2 is a graph showing the shock absorbing capabilities of a configuration made of only spacer fabric.
Figure 3:
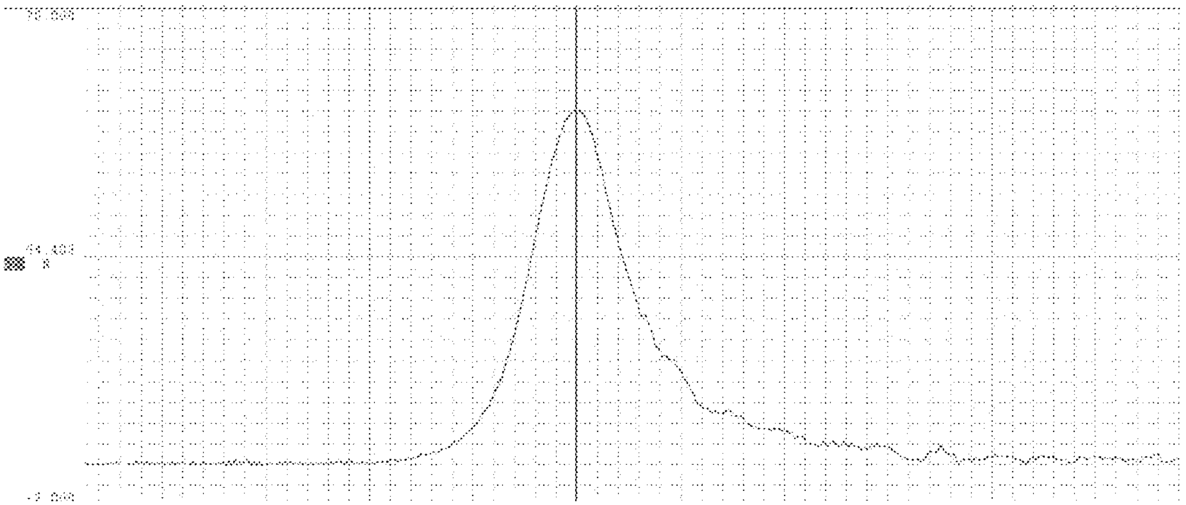
FIG. 3 is a graph showing the shock absorbing capabilities of silicone used in prosthetic socks and liners.
Figure 4:
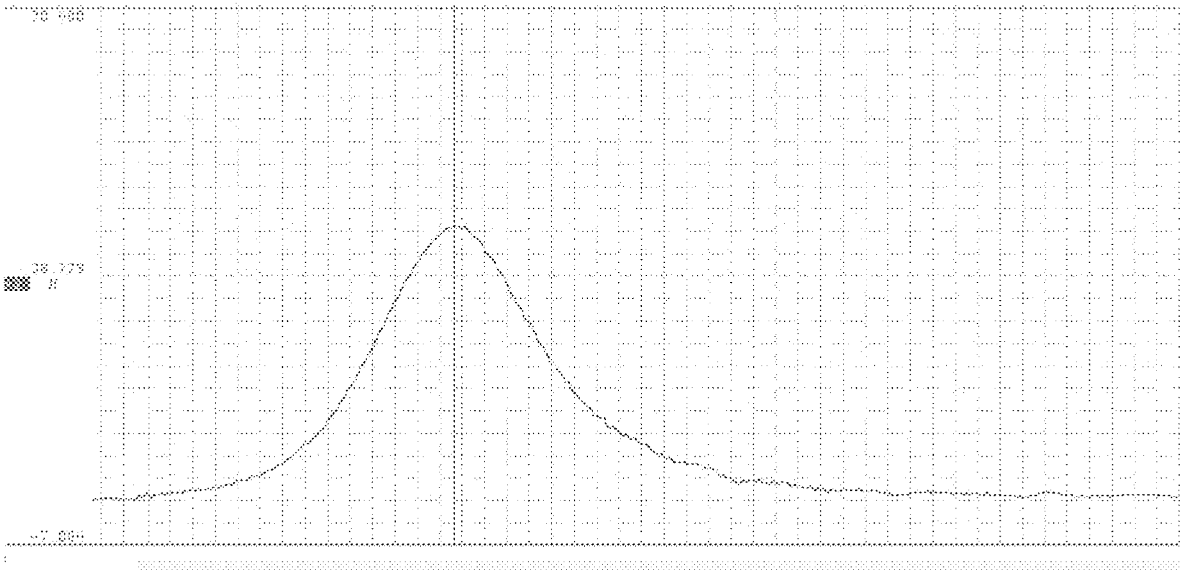
FIG. 4 is a graph showing the shock absorbing capabilities of a composite material of silicone liner with spacer fabric.
Figure 5:
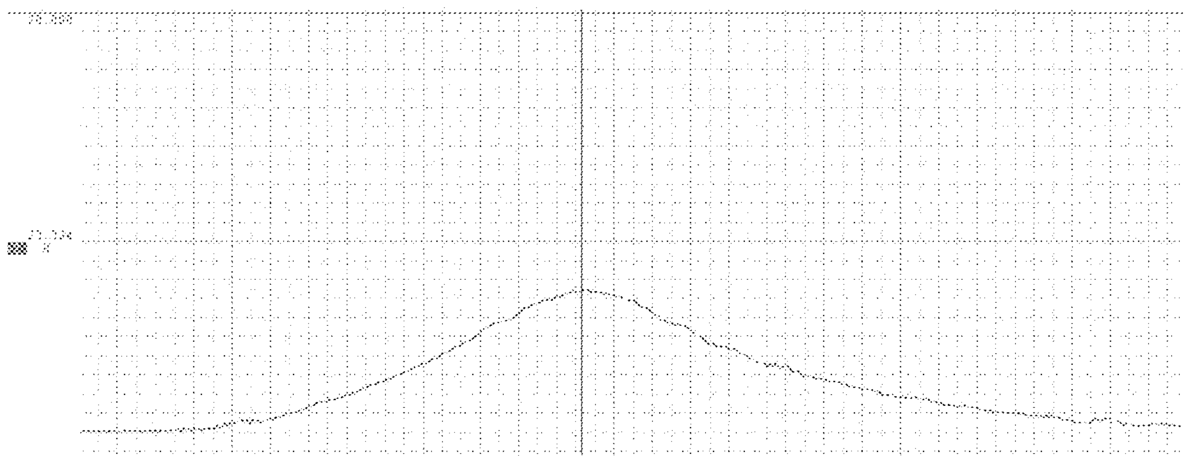
FIG. 5 is a graph showing the shock absorbing capabilities of a prosthetic liner comprising a thermoplastic elastomer gel and fabric without spacer fabric.

A first test was performed, as seen in FIG. 1, against the leather strike face with no material between the strike face and the anvil. As can be seen from the graph, the force generated from the strike is at a maximum. A second test was performed, as seen in FIG. 2, against a test material made solely of spacer fabric 18. This resulted in a force of roughly 55 Newtons being transferred through the material. A third test was performed, as seen in FIG. 3, using only the silicone material that is used in standard prosthetic socks and liners. This test resulted in a force of over 60 Newtons being transferred through the material. A fourth test was performed, as seen in FIG. 4, using a composite material incorporating the spacer fabric 18 with the silicone used in the third test which resulted in a force of only about 40 Newtons being transferred through the material. A fifth test, as seen in FIG. 5, generated a force of less than 20 Newtons when standard thermoplastic elastomer gel (SEEPS, SEBS, SEPS-type materials) was tested.

Figure 6:
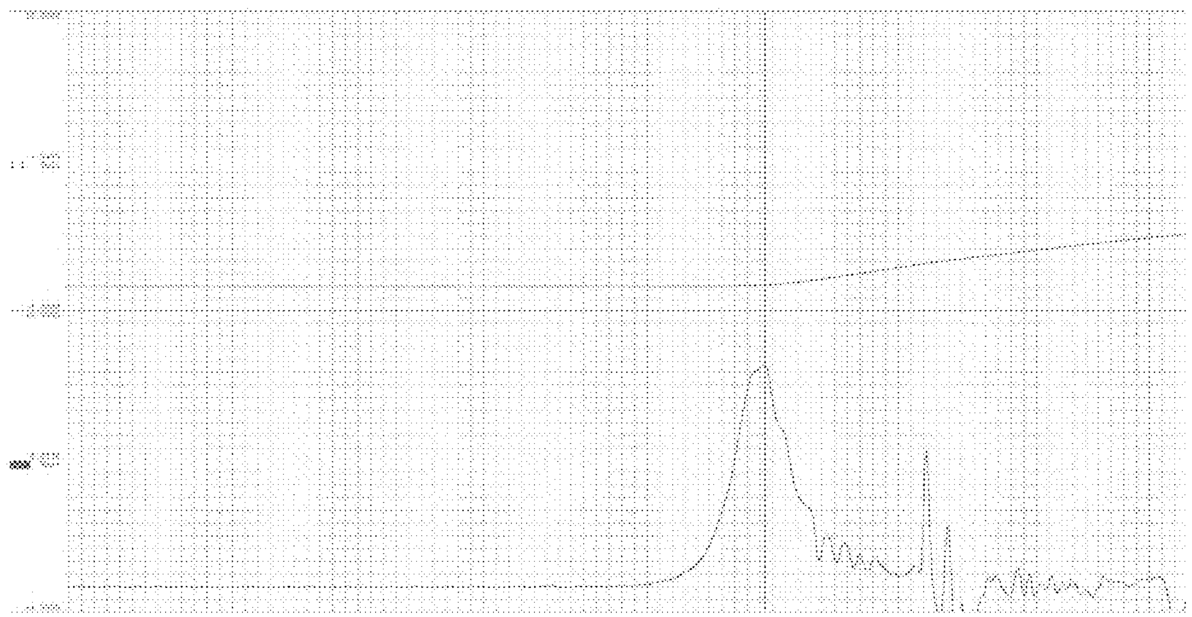
FIG. 6 is a graph showing the shock absorbing capabilities of a standard 5-ply cotton sock.

Further tests were performed on a variety of materials as shown in FIGS. 6-9. These tests produced results showing the voltage created from the anvil hitting the striker through various materials. A sixth test, as shown in FIG. 6, was run against a 5-ply cotton prosthetic sock having no spacer fabric which generated a voltage of nearly 10 volts through the impulse of the anvil striking the leather striker using gravity. Voltage can be converted to force using standard conversions known to those of skill in the art. The cotton sock for this test was cut to a 3.5-inch diameter to fit onto the striker and dropped solely using gravity.

Figure 7:
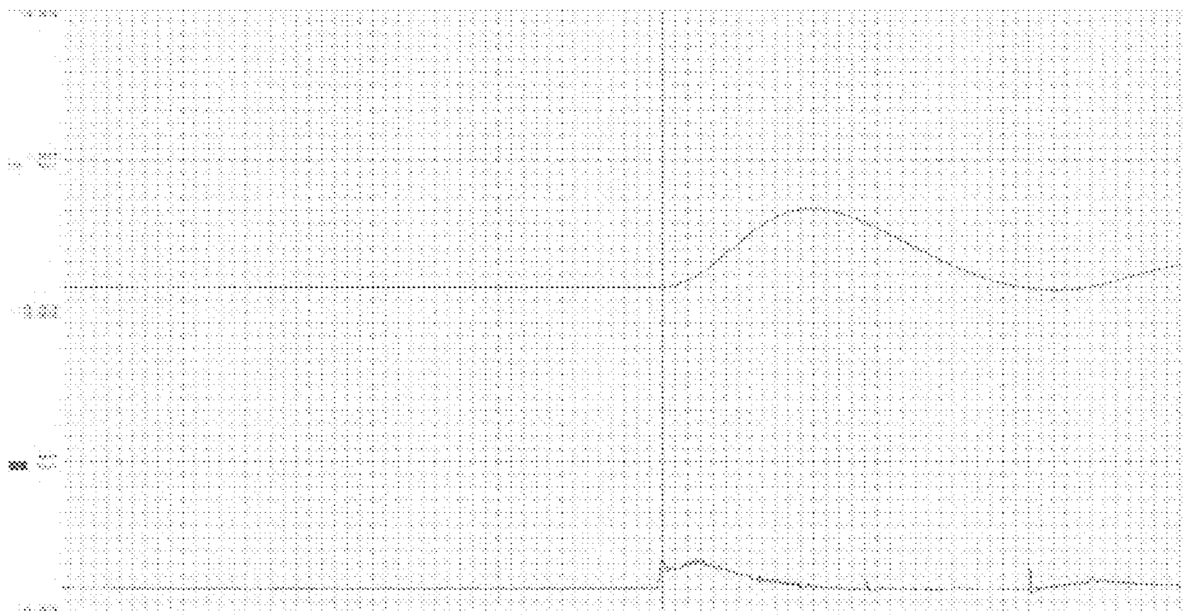
FIG. 7 is a graph showing the shock absorbing capabilities of a sock made with memory foam.

At the opposite end of the spectrum, as shown in FIG. 7, the same force test was performed on a liner where the distal end comprised memory foam, otherwise described as urethane open cell ultra-soft foam, having a density of 6 pounds per cubic foot. As seen in FIG. 7, a negligible force was created from the force of dropping the anvil on a liner using memory foam. However, this configuration for a liner is not suggested as memory foam does not breathe nor does it wick moisture away. Likewise, memory foam has a very slow rebound rate which is undesirable for quick impact activities like running or jumping. Furthermore, such a configuration cannot be washed using a conventional washing machine.

Figure 8:
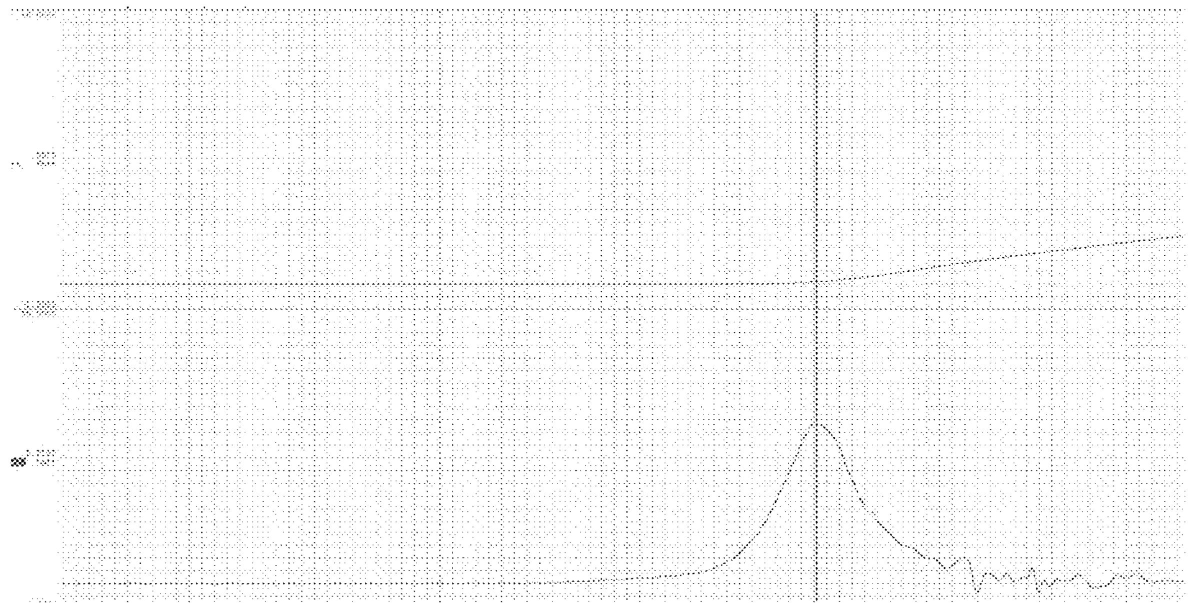
FIG. 8 is a graph showing the shock absorbing capabilities of a sock made using a spacer fabric of a first configuration.
Figure 9:
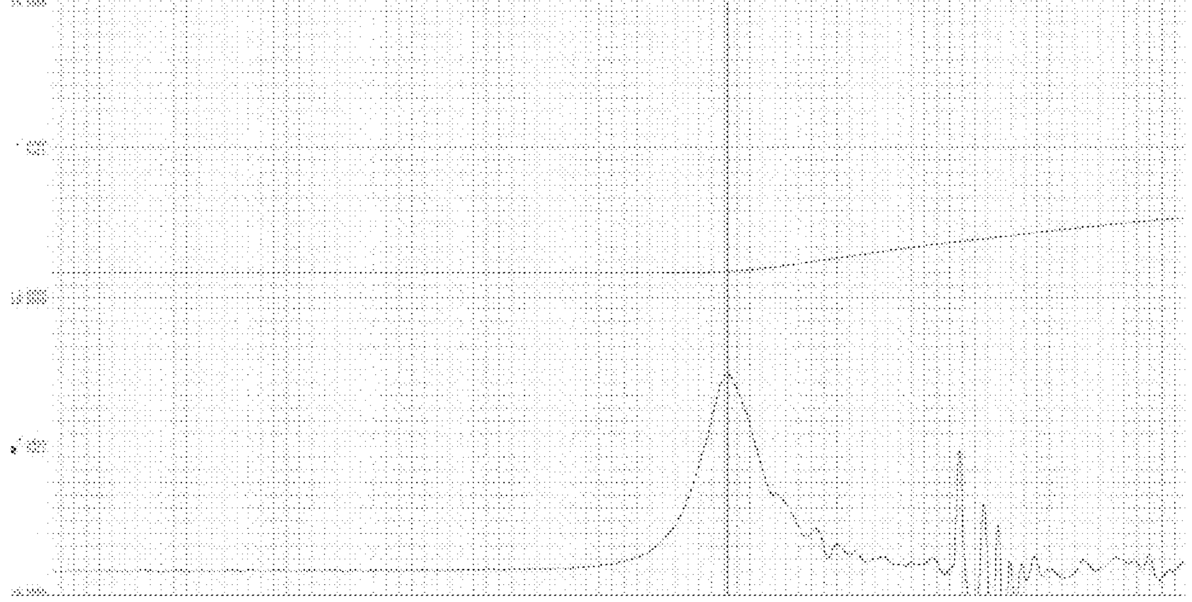
FIG. 9 is a graph showing the shock absorbing capabilities of a sock made using a spacer fabric of a second configuration.
Figure 10:
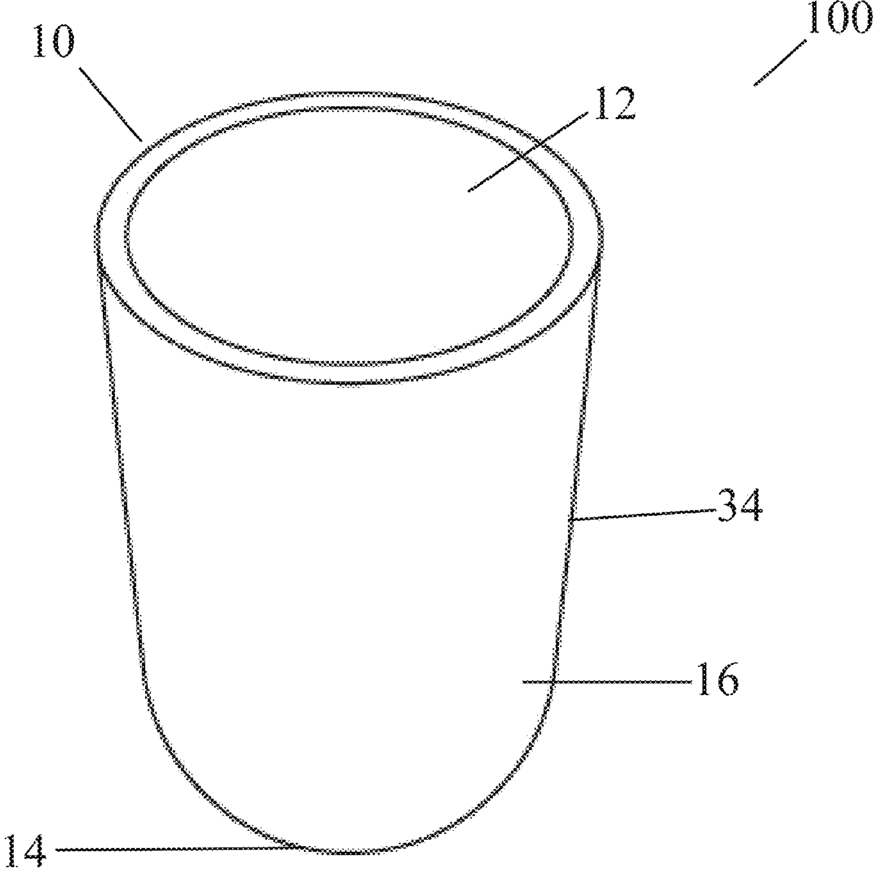
FIG. 10 is a perspective view of a prosthetic liner of the present invention.

Thus, it is preferred that spacer fabric be used so as to create the maximum reduction in force on a limb while at the same time allowing for breathability, moisture wicking, and reduction in weight. As seen in FIGS. 8 and 9, utilizing spacer fabric results in decreased force dispersed through the liner. Specifically, as shown in FIG. 8, running the test using spacer fabric with two ends of polyester and three ends of monofilament distance fibers having a thickness of 0.12 millimeters along with 0.5 inch tufts results in a voltage of about 6 volts. The polyester used is primarily dependent on machine gauge; a smaller gauge machine will use a finer filament, as an example, which will consequently affect thickness and tuft length as known by those of skill in the art. As shown in FIG. 9, running the test using spacer fabric with two ends of polyesters and one end of monofilament distance fibers having a thickness of 0.12 millimeters and one inch tufts results in a voltage of about 8 volts. In both cases, the amount of force imparted through the sock/liner was less than in the standard cotton sock/liner. The fabric is preferably made of polyester but may be any knittable filament that wicks moisture from surfaces such as Coolmax® or nylon as well as other natural or synthetic fibers. Knittable filament means a filament now known or later developed capable of being knitted.

For the present invention, as can be seen in FIGS. 10-13, the configuration may be that of a prosthetic liner 100 that has a liner proximal end 10 having an opening 12, a closed liner distal end 14, and sidewalls 34. The distal end 14 further comprises a distal region 16 that is knitted with spacer fabric 18 to the same circumference as the liner 100. Spacer fabric 18 preferably extends through the entirety of the distal region 16 and tapers as it approaches the end of the distal region 16. The remainder of the liner 100 can be made of any other material 84 as desired by the user, such as textile, given that those areas of the liner do not get imparted with the same pressure shock that comes with ambulation. Alternatively, as shown in FIG. 6, the liner 100 may be made entirely out of the spacer material 18, meaning from the distal end 14 to the proximal end 10 and including the sidewalls 34, because some pressure shock may still be imparted to the residual limb during ambulation. Likewise, in another alternative embodiment as shown in FIG. 8, the liner 100 may include spacer material 18 in only the distal region 16 on a first half 86 (as defined by the diameter of the liner 100) and as the entirety of the sidewalls 34 of a second half 88.

Figure 14:
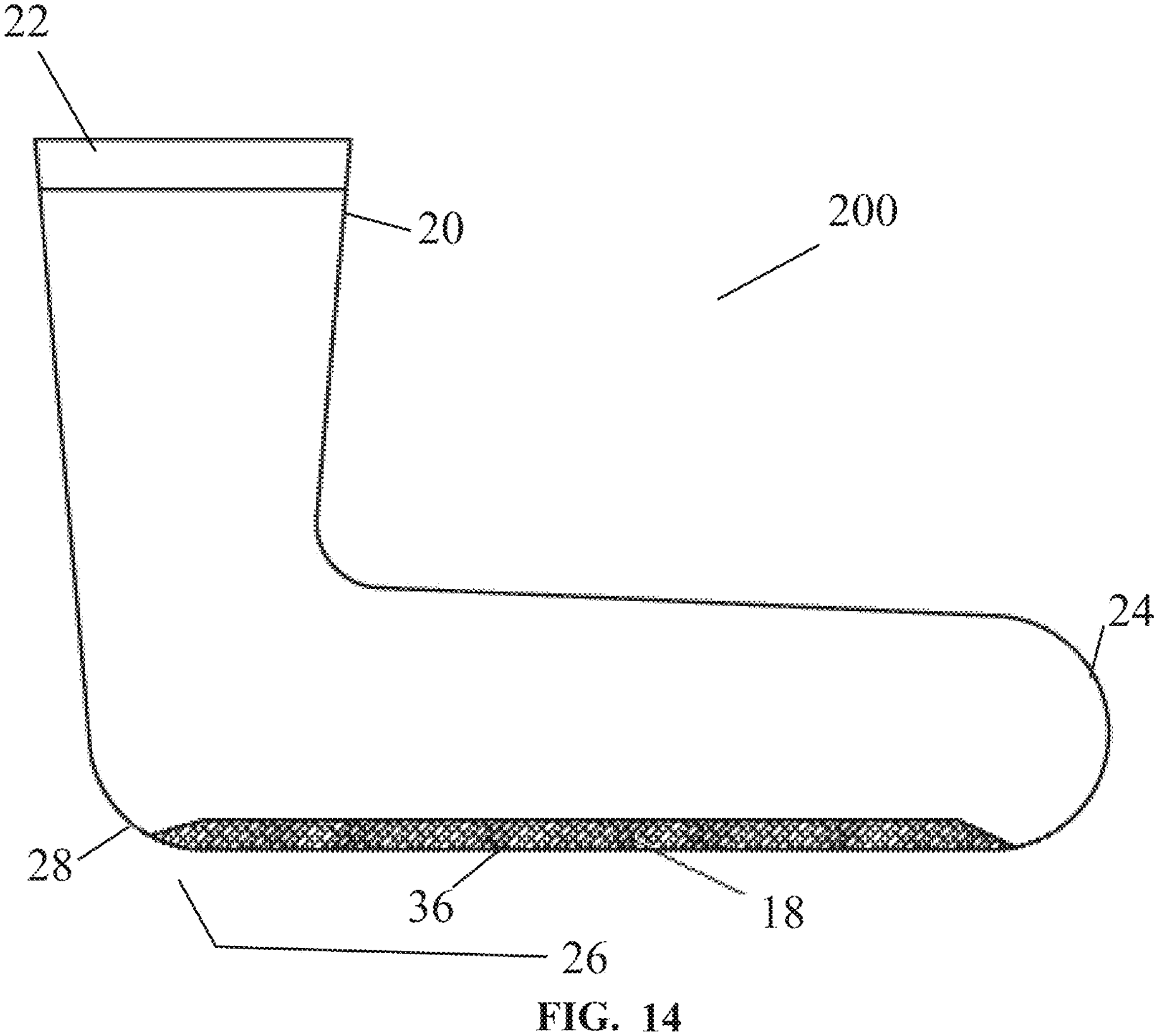
FIG. 14 is a cross-sectional view of a sock of the present invention.
Figure 15:
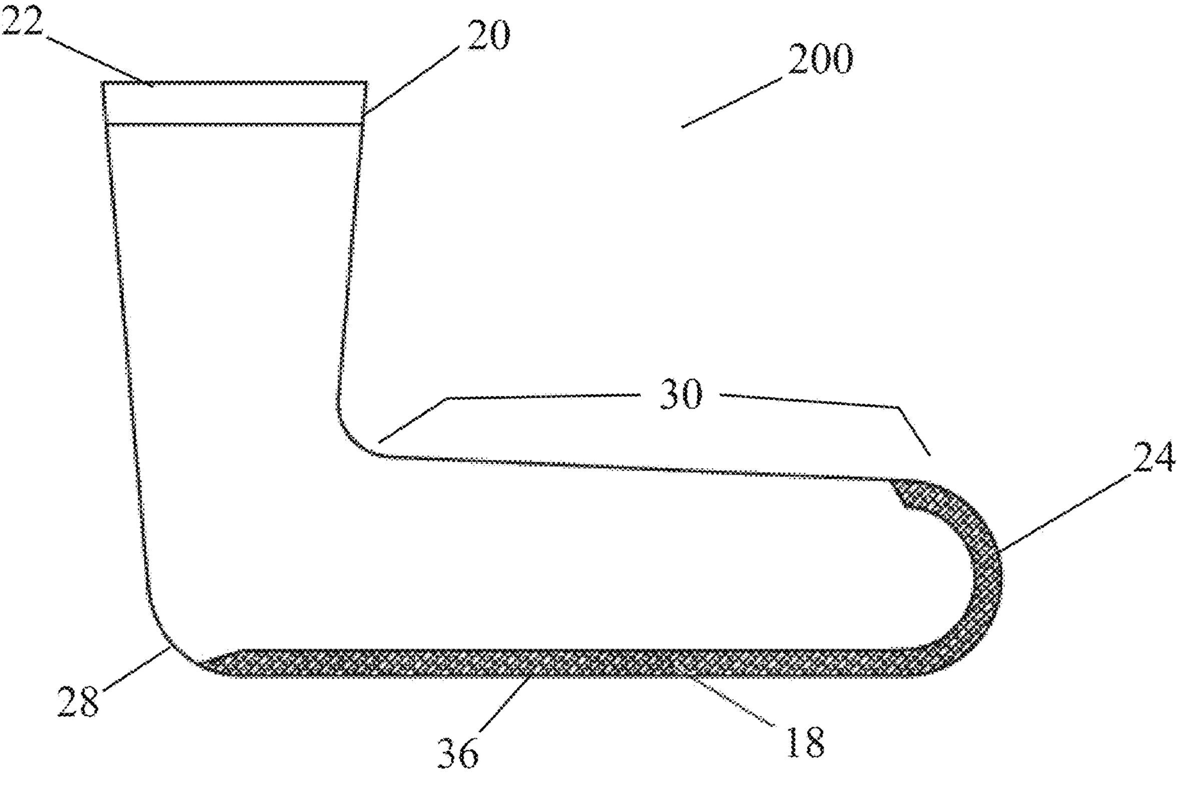
FIG. 15 is a cross-sectional view of an alternative embodiment of a sock version of the present invention.
Figure 16:
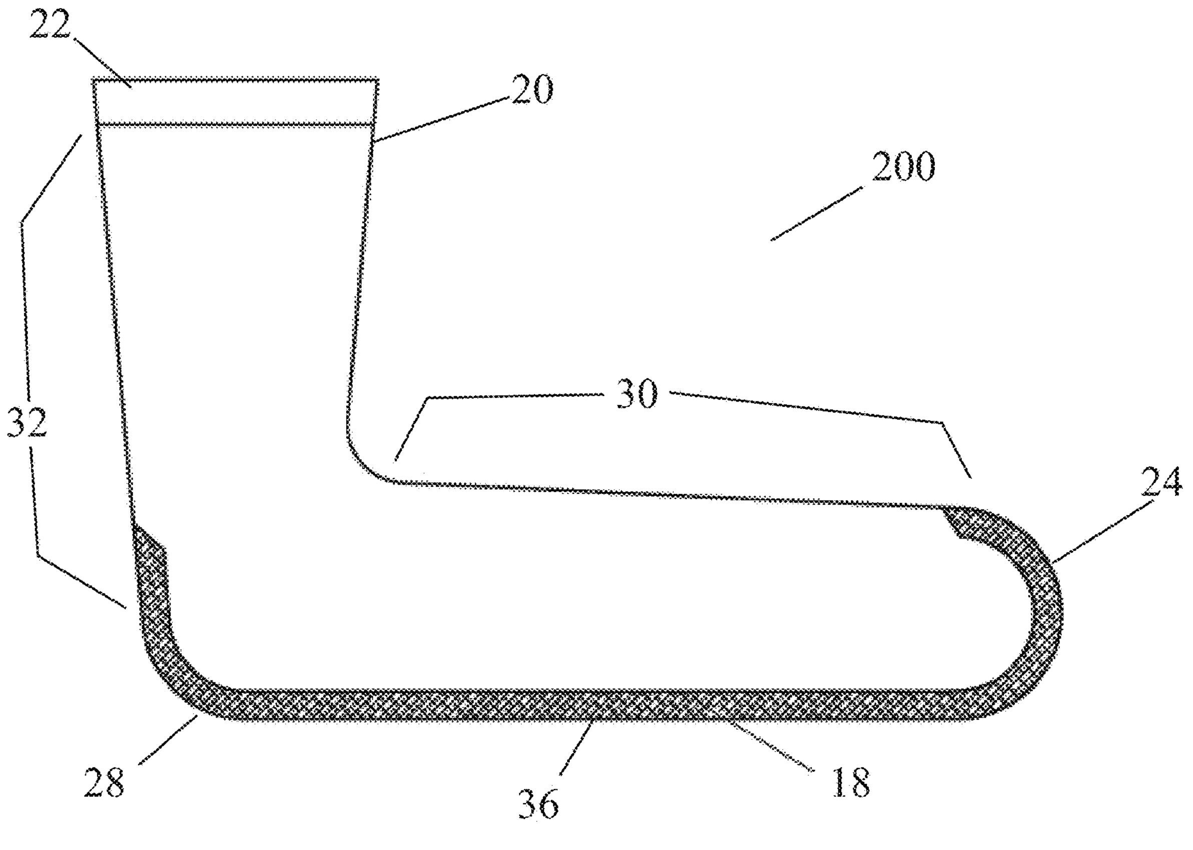
FIG. 16 is a cross-sectional view of an alternative embodiment of a sock version of the present invention.

Likewise, as seen in FIGS. 14-16, a sock 200 has a sock proximal end 20 having a sock opening 22 and a closed sock distal end 24. The spacer fabric 18 can be in a variety of different configurations when used with a sock 200 as opposed to a liner 100. As seen in FIG. 14, the sock 200 may have spacer fabric 18 along a mid-foot region 26 that extends near, but not around, the sock distal end 24 to a heel region 28. This spacer fabric 18 orientation provides support to the archway of a foot.

An alternative orientation is provided in FIG. 15 wherein the spacer fabric 18 curves around the sock distal end 24 to a top sock face 30 but does not extend throughout the entirety of the top sock face 30 as that would be unnecessary for the purposes of the present invention. Finally, as shown in FIG. 16, the spacer fabric 18 extends from the top sock face 30, through the mid-foot region 26, and finishes past the heel region 28 up a portion of a back heel region 32. The amount the spacer fabric 18 extends upwardly through this back heel region 32 depends on the preference of the user but does not extend through the entirety of the back heel region 32 because, as with the previous example, it would be unnecessary for the purposes of the present invention in preventing pain or discomfort.

Figure 17:
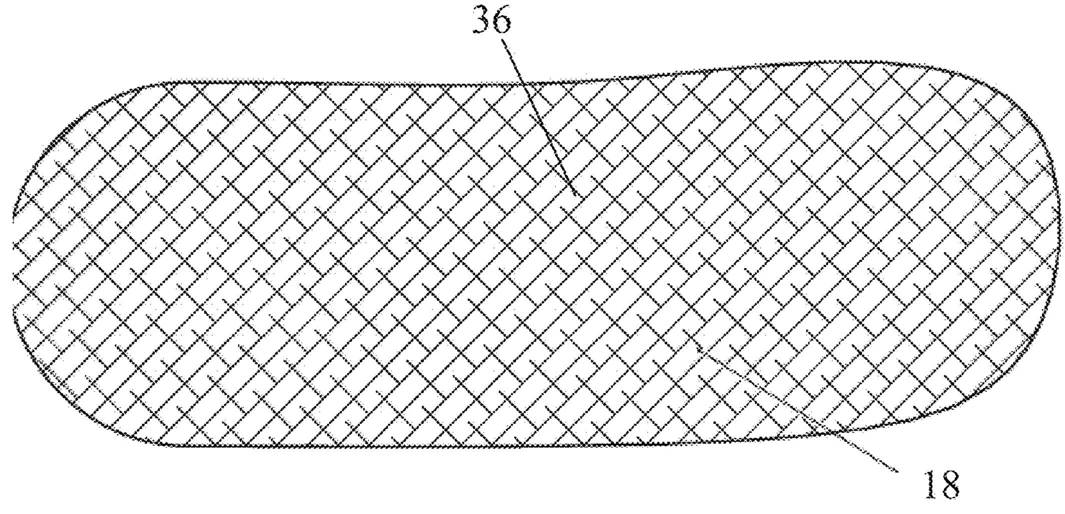
FIG. 17 is a top view of spacer fabric arrangement used with the sock of the present invention.
Figure 18:
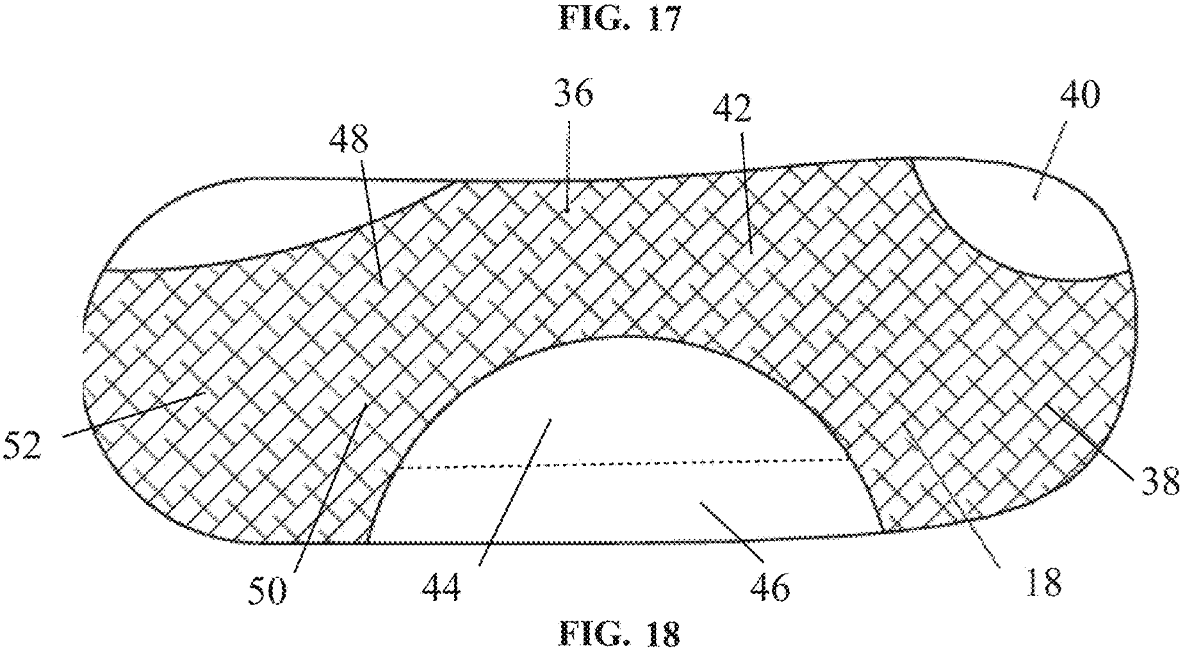
FIG. 18 is a top view of an alternative spacer fabric arrangement used with the sock of the present invention.

As shown in FIGS. 17 and 18, the spacer fabric 18 for sock 200 is preferably in one of two configurations. The first comprises spacer fabric 18 throughout the entirety of the bottom face 36 of the sock 200, as shown in FIG. 17. The second configuration, as shown in FIG. 18, comprises spacer fabric 18 in select regions along the bottom face 36; specifically, (1) the toe region 38 leaving out the big toe (hallux) region 40, (2) the metatarsal head (MTH) 1 region 42 leaving out the MTHs 2-3 region 44 and the MTHs 4-5 region 46, (3) the medial mid-foot region 48, (4) the lateral mid-foot region 50, and (5) the lateral heel region 52 leaving out the medial heel region 54. This second configuration focuses on the regions of the foot that face increased pressure during ambulation and the addition of spacer fabric contributes to a lessening of pain and discomfort in those regions during use. However, the spacer fabric 18 may be found solely in the back heel region 32, solely in the metatarsal head 1 region 42 and medial mid-foot region 48 or solely in the toe region 38. In all configurations, the spacer fabric 18 has a thickness between 3 millimeters and 16 millimeters, preferably between 4.5 and 9 millimeters, as compared to the areas of the sock 200 or liner 100 that do not comprise spacer fabric 18 which is preferably between 1 and 10 millimeters thick.

Furthermore, it is known that sensors can aid users in determining where the highest pressure points during their stride exist. The present invention may also incorporate wireless sensors that can communicate via Bluetooth or other wireless signals so as to inform a user about their stride characteristics. Due to the structure of the spacer fabric 18, described below, incorporation of these sensors will not bother a user unlike the incorporation of sensors into standard socks.

During the knitting process of the spacer fabric 18, the knitting must create an inner wall 56 and an outer wall 58 for the tubular shape of the spacer fabric 18 with an inner support structure 60. The preferred knit structure for liners has four total layers: the front outer face 62, the front inner face 64, the back inner face 66, and the back outer face 68. The support layers run between the inner wall 56 and the outer wall 58 to provide the shock absorbing qualities to the spacer fabric 18. Tufts are made during the knitting courses to support the fabric and provide additional absorbing qualities by anchoring the layers together. All of these attributes can be adjusted to control the distance between the layers, the feel of the fabric, and the shock absorbing qualities.

Figures 19, 20:
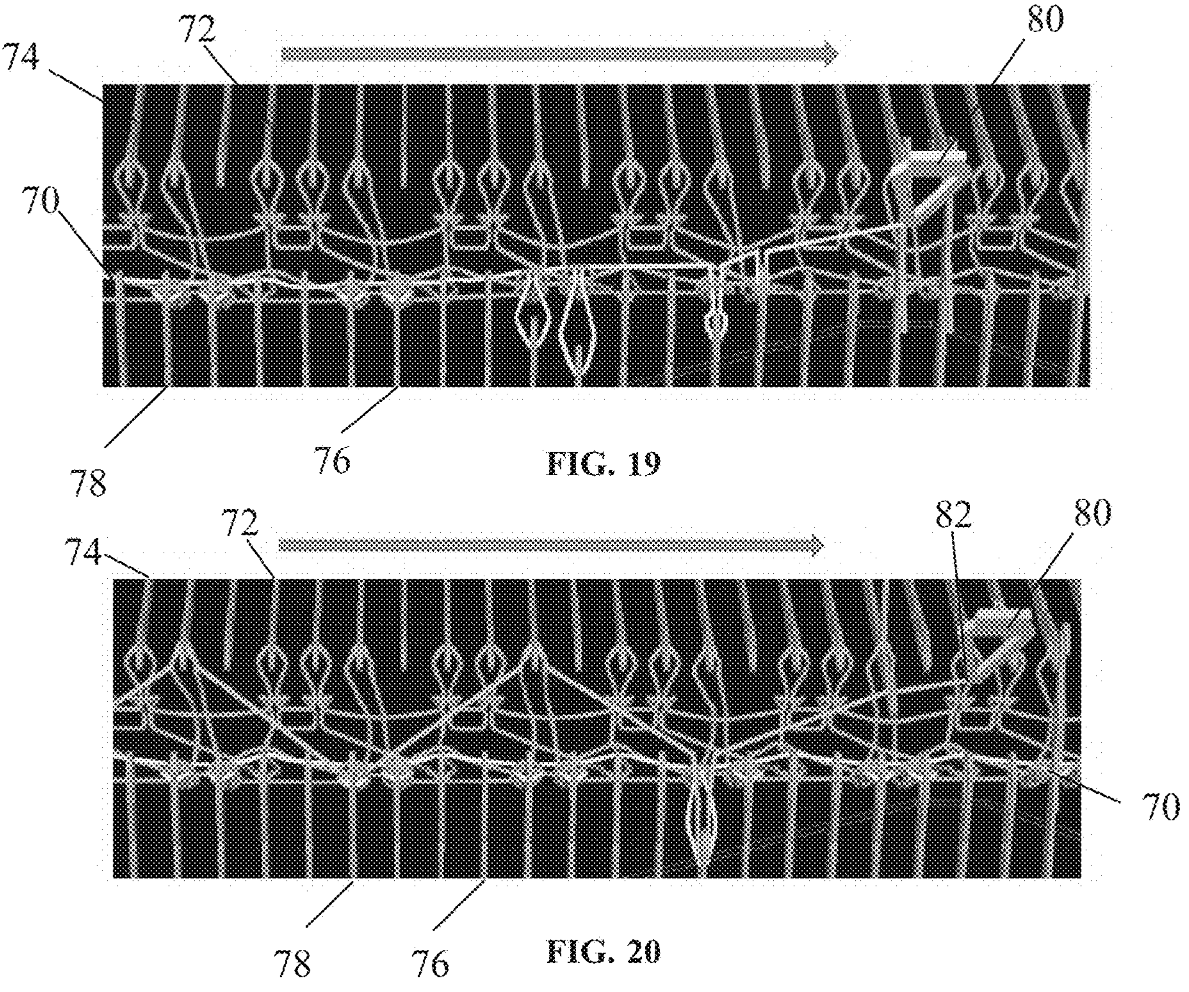
FIG. 19 is a perspective view of a knitting machine performing the first step of creating the spacer fabric to be used with the present invention.
FIG. 20 is a perspective view of a knitting machine performing the second step of creating the spacer fabric to be used with the present invention.
Figures 21, 22:
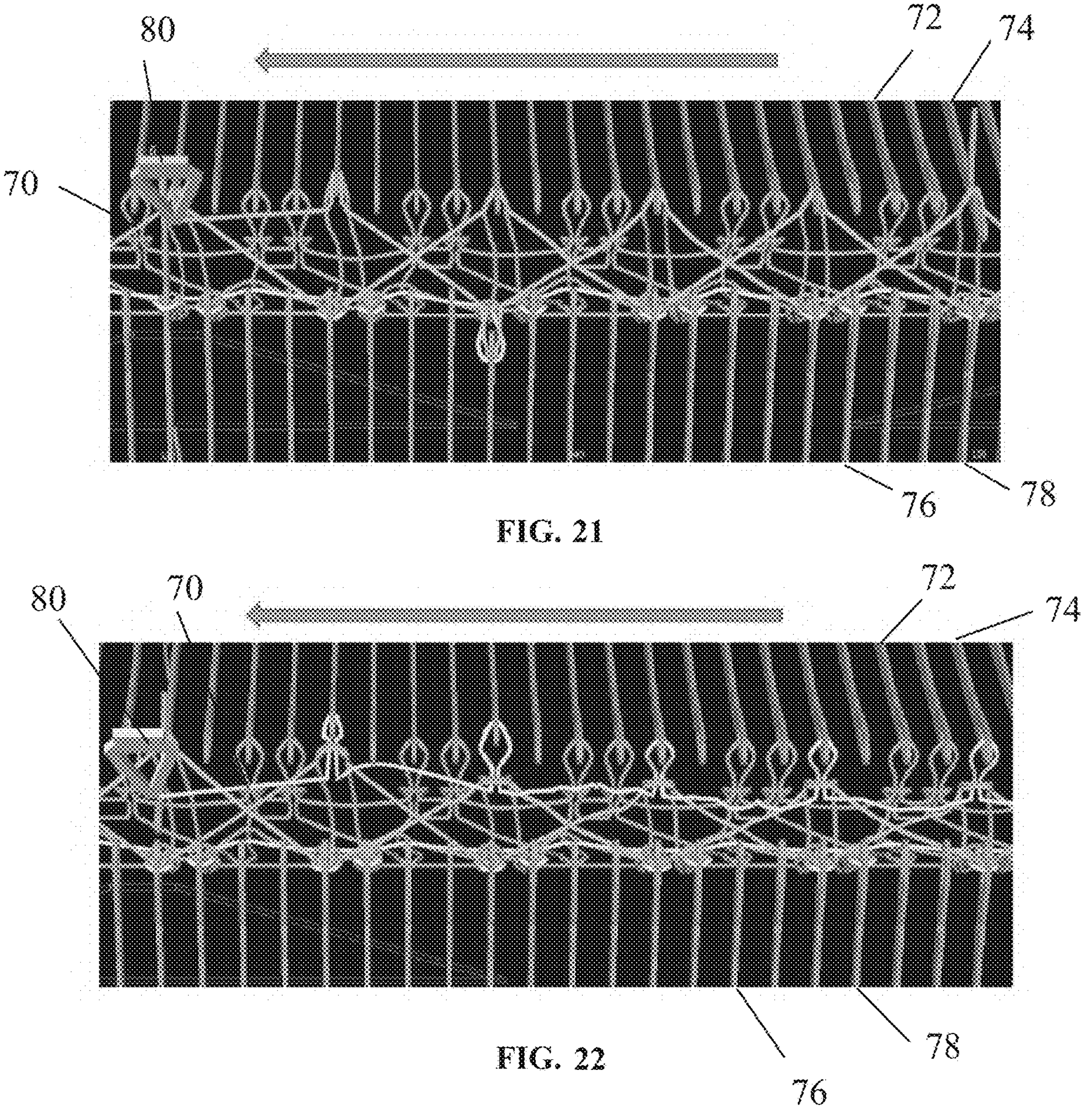
FIG. 21 is a perspective view of a knitting machine performing the third step of creating the spacer fabric to be used with the present invention.
FIG. 22 is a perspective view of a knitting machine performing the fourth step of creating the spacer fabric to be used with the present invention.

Preferably, as shown in FIGS. 19-31, the spacer fabric 18 is a 2×2 knit outer wall 56 with a 1×3 inner wall 58. The process begins by knitting the preferred yarn 70, for example polyester, in a two by two pattern which means looping the yarn through two front members 72 of a front needle bed 74 and then skipping two needles before resuming knitting two front members on the front needle bed 76 (FIG. 19) and then tucking the monofilament 82 between the front needle bed 74 and rear needle bed 78 with the carrier 80 shifting in a first direction (FIG. 20). This pattern is then repeated but the carrier going in the opposite direction and tucking on needles mirroring the prior step (FIG. 21) which is then knit on the rear needle bed 78 using rear members knitting a 1×3 pattern using the rear needle bed (FIG. 22) and which completes one course of tubular fabric for the front outer face 62 and the front inner face 64 of the sock 200.

Figures 1, 11:
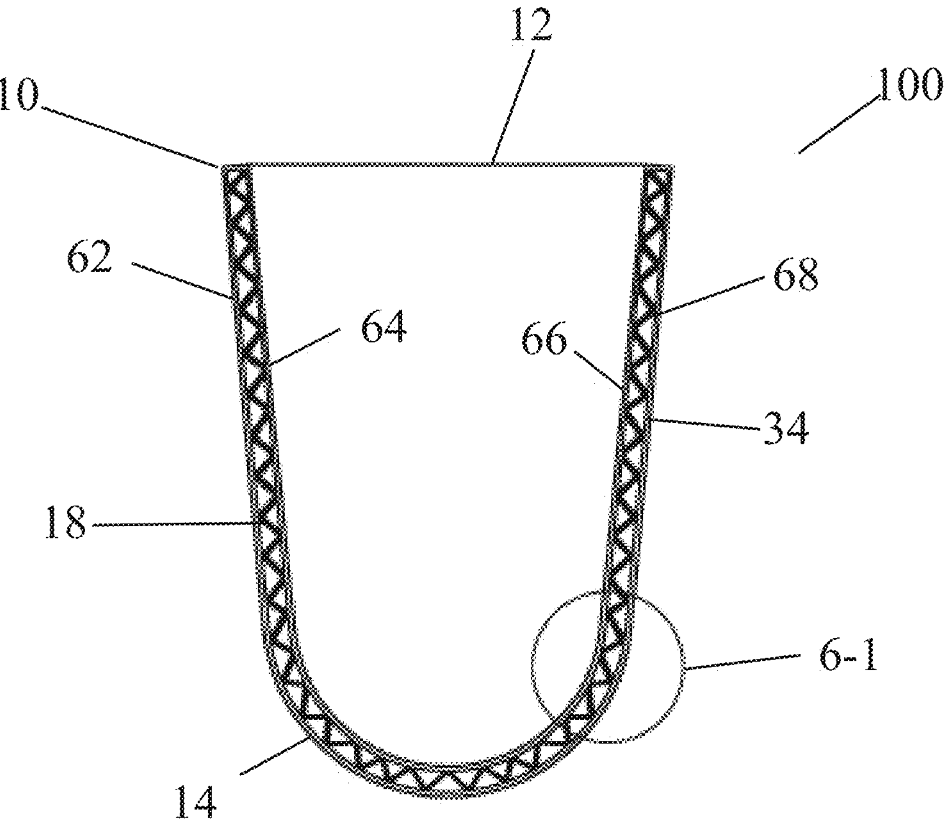
FIG. 11 is a cross-sectional view of a prosthetic liner of the present invention.
Figure 12:
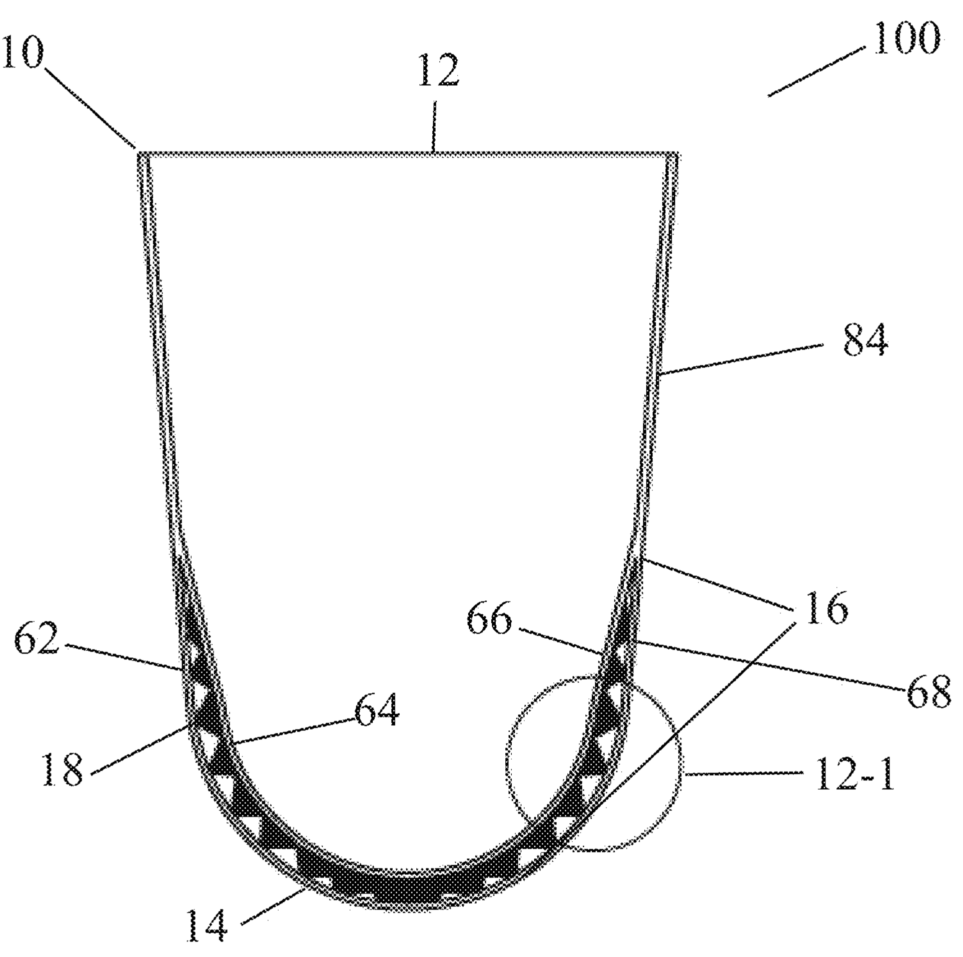
FIG. 12 is a cross-sectional view of an alternative embodiment of a prosthetic liner version of the present invention.
Figures 1, 12:
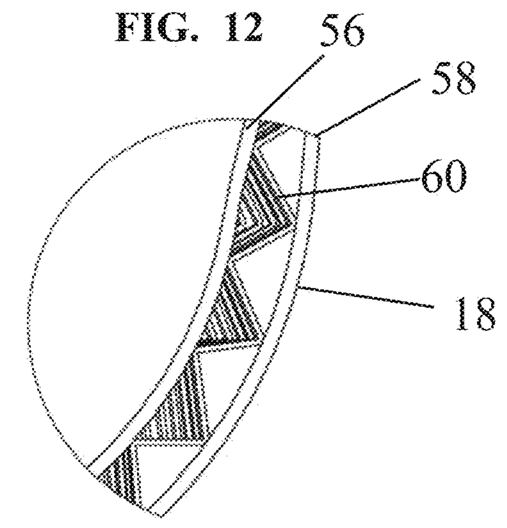
Figure 13:
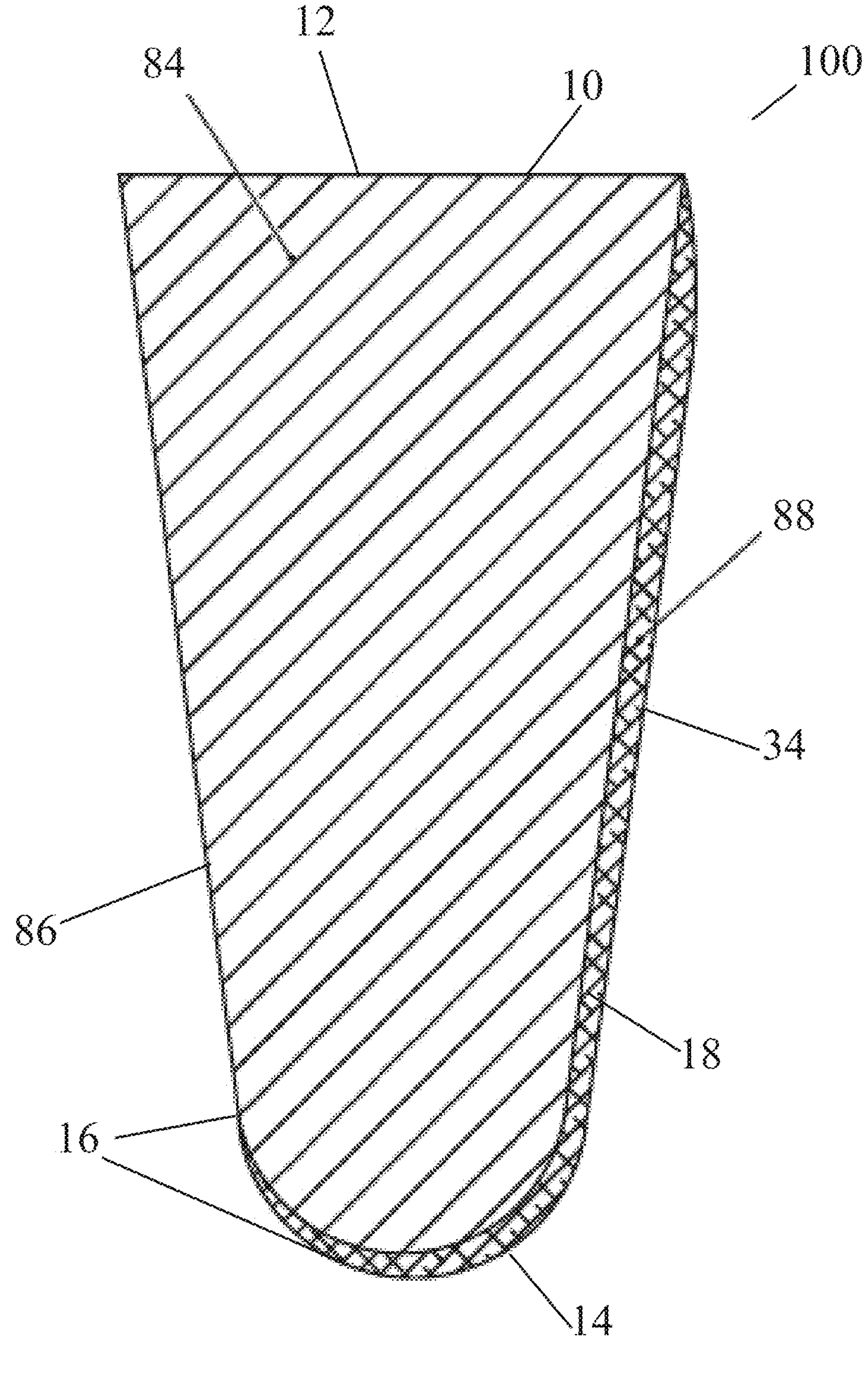
FIG. 13 is a cross-sectional view of an alternative embodiment of a prosthetic liner version of the present invention.
Figures 23, 24:
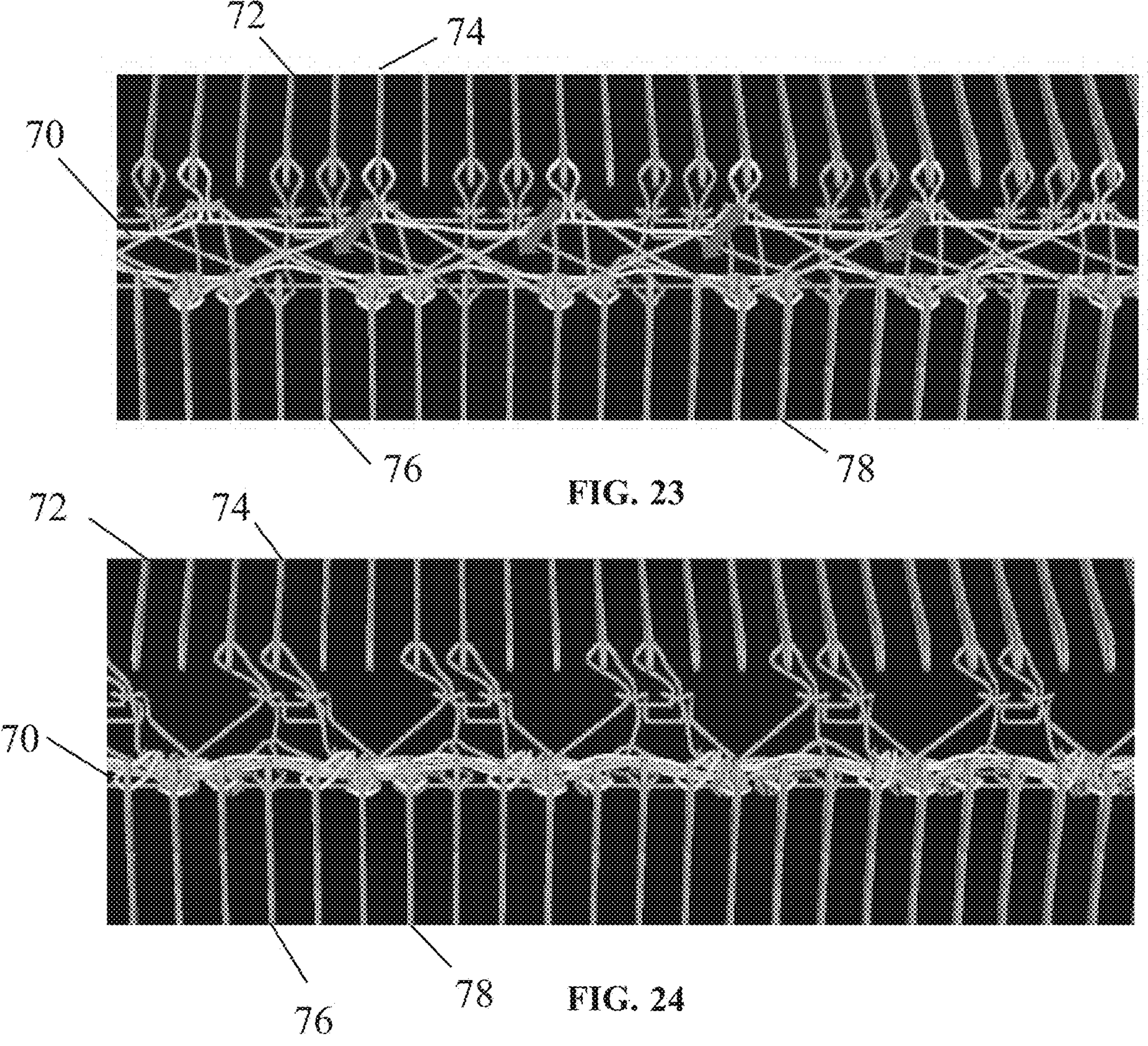
FIG. 23 is a perspective view of a knitting machine performing the fifth step of creating the spacer fabric to be used with the present invention.
FIG. 24 is a perspective view of a knitting machine performing the sixth step of creating the spacer fabric to be used with the present invention.
Figures 25, 26:
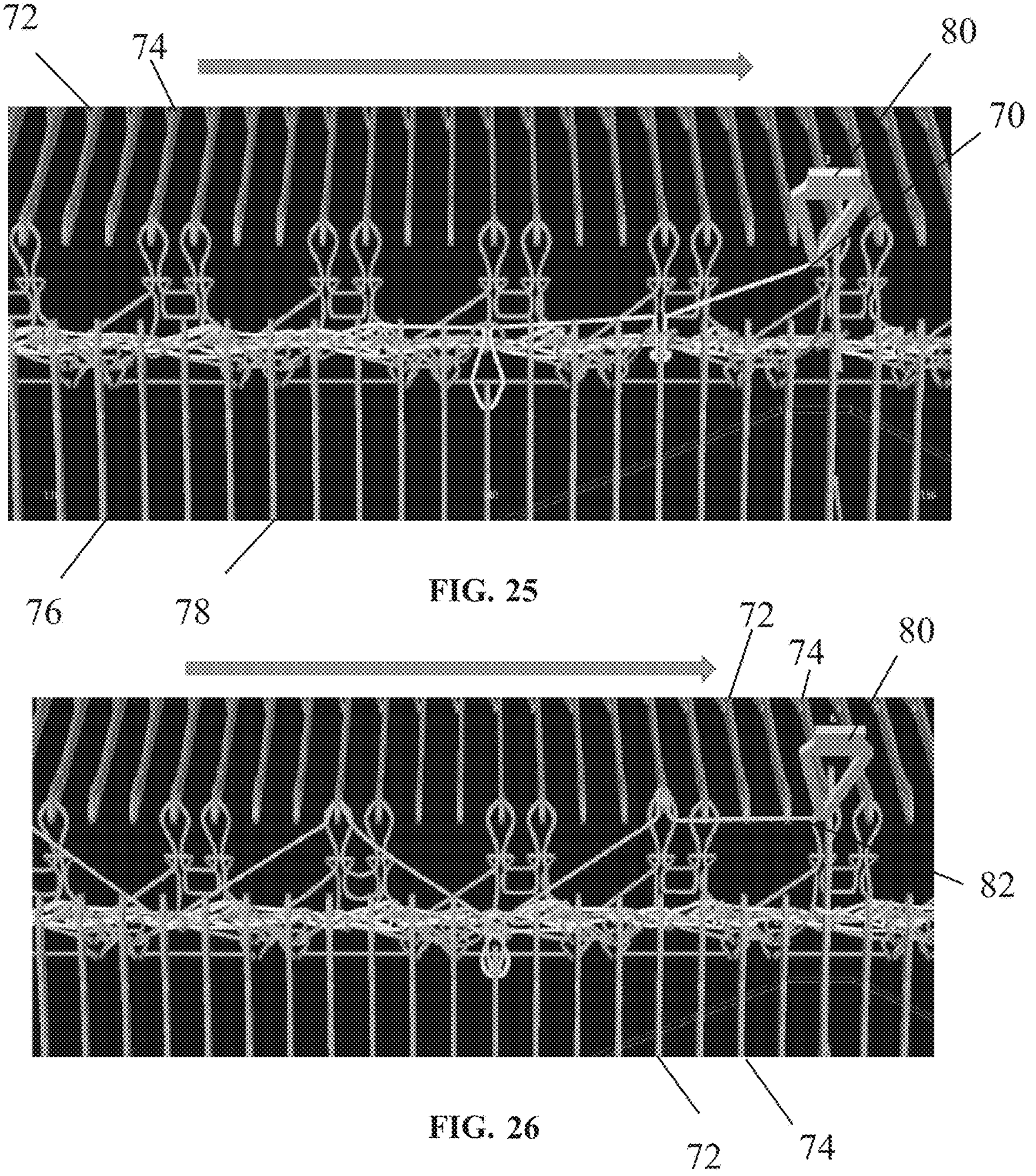
FIG. 25 is a perspective view of a knitting machine performing the seventh step of creating the spacer fabric to be used with the present invention.
FIG. 26 is a perspective view of a knitting machine performing the eighth step of creating the spacer fabric to be used with the present invention.
Figures 27, 28:
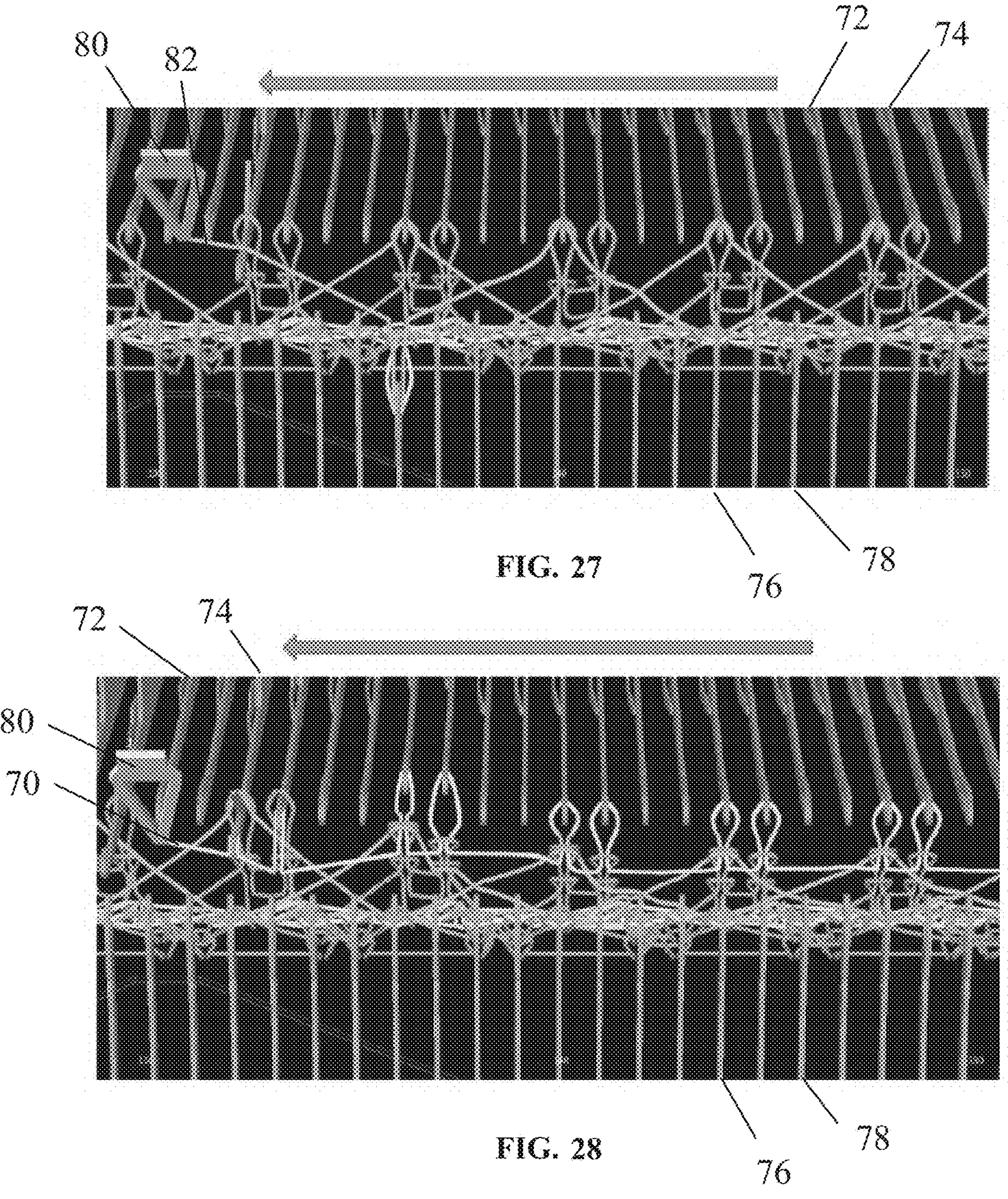
FIG. 27 is a perspective view of a knitting machine performing the ninth step of creating the spacer fabric to be used with the present invention.
FIG. 28 is a perspective view of a knitting machine performing the tenth step of creating the spacer fabric to be used with the present invention.
Figures 29, 30:
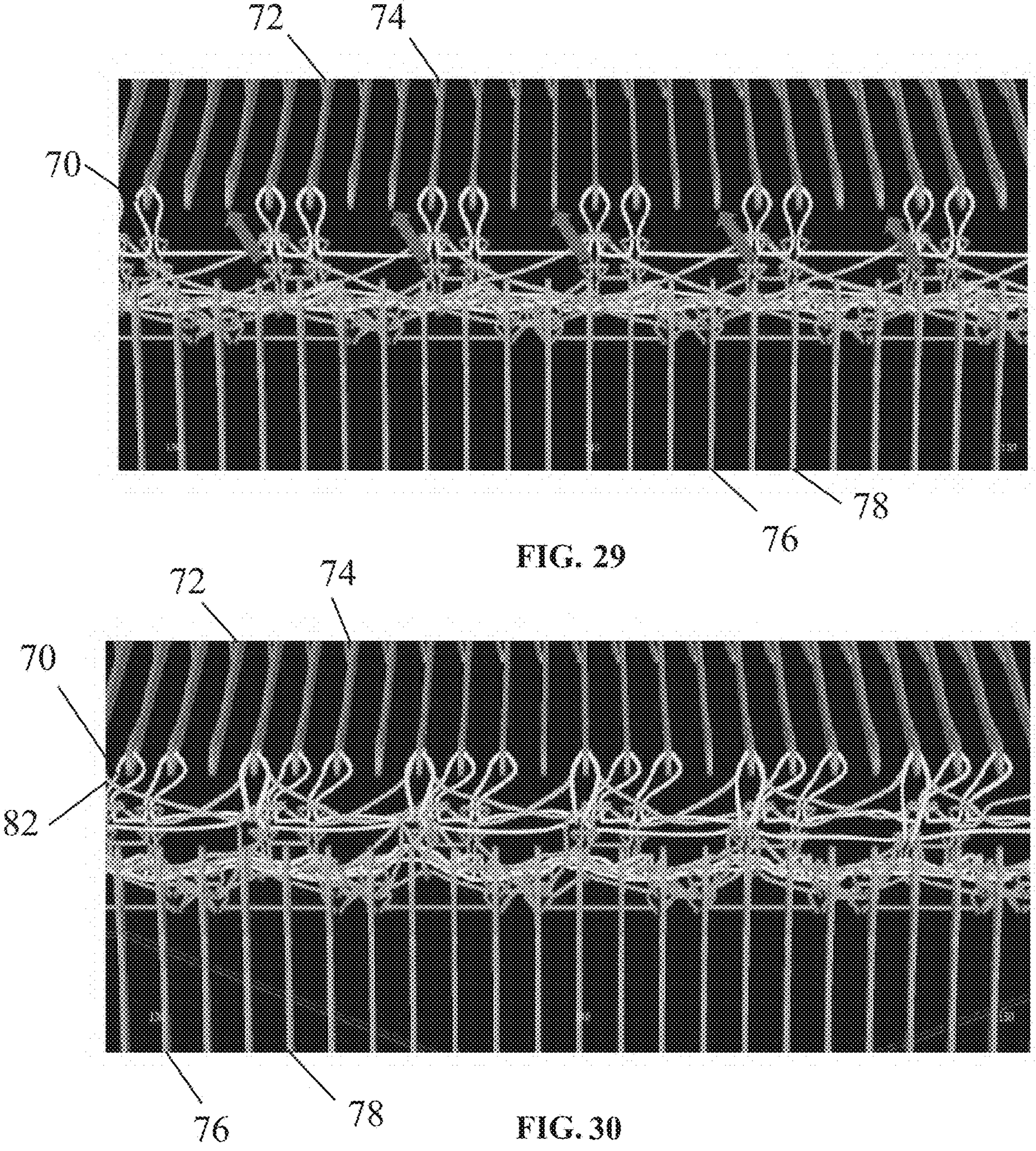
FIG. 29 is a perspective view of a knitting machine performing the eleventh step of creating the spacer fabric to be used with the present invention.
FIG. 30 is a perspective view of a knitting machine performing the twelfth step of creating the spacer fabric to be used with the present invention.
Figure 31:
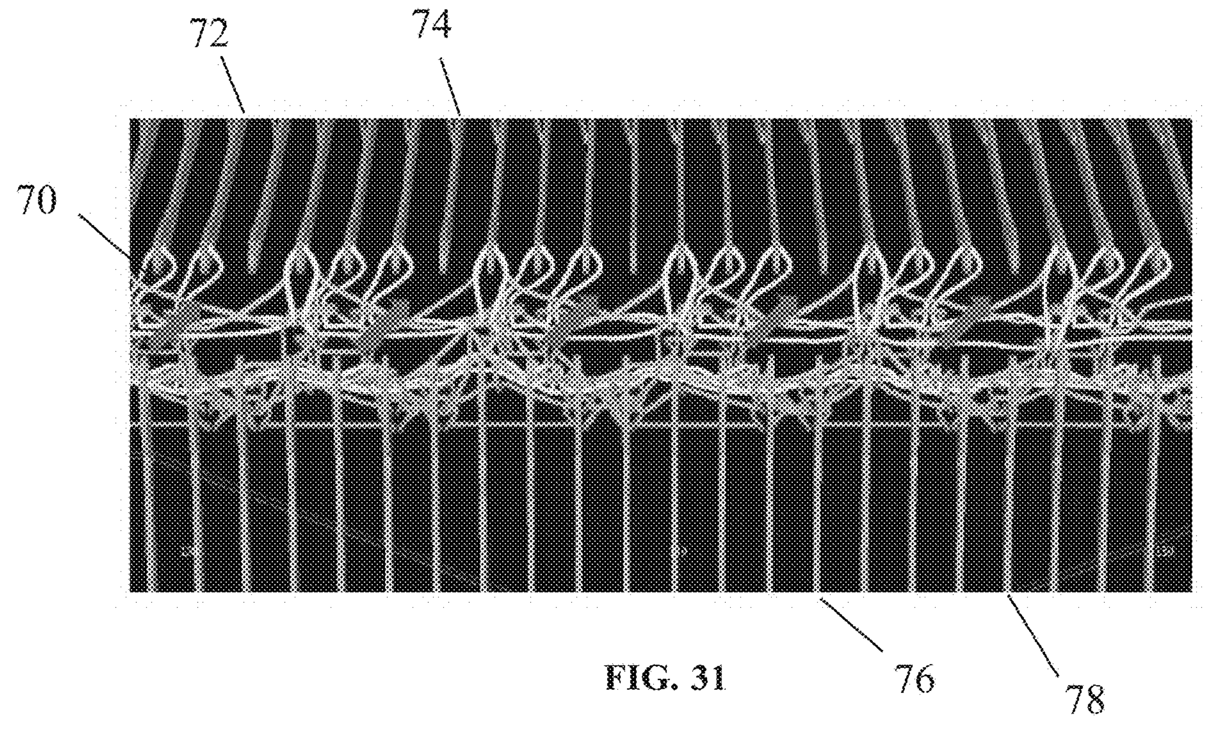
FIG. 31 is a perspective view of a knitting machine performing the thirteenth step of creating the spacer fabric to be used with the present invention.

The inner wall 56 portion then gets transferred onto an empty needle to get both the inner wall 56 and outer wall 58 onto the front needle bed 74 to begin knitting the back inner face 66 and the back outer face 68 (FIGS. 23 and 24). The yarn 70 is then knit in a one by three pattern (i.e. through one front member 72 and three rear members 76) creating the back inner face 66 (FIG. 25). The monofilament then gets tucked between the front needle bed 74 and the rear needle bed 78 (FIG. 26) specifically between the first needle of the two by two pattern on the rear needle bed 78 and the first needle to the right of the front needle bed 76 with the carrier 80 shifting in a first direction. This pattern is repeated with the carrier 80 traveling in the opposite direction with the monofilament 82 (FIG. 27). The yarn 70 is then knit in a two by two pattern (FIG. 28) on the rear needle bed 78 which creates the back inner face 66 and which completes one full course of the front inner face 64 and the back outer face 66. The back outer face 66 is then transferred onto an empty front left needle from the two by two pattern on the front needle bed 74 (FIG. 29) which then makes it so that all fabric for the inner wall 56 is on the front needle bed 74 while all of the fabric for the outer wall 58 is on the rear needle bed 78 (FIG. 30). Finally, the fabric on the front needle bed 74 gets transferred to the rear needle bed 78 so the process can be repeated until the desired amount of knitting has been completed (FIG. 31). The resulting pattern is shown in FIGS. 11-1 and 12-1. This knitting style allows for the creation of three-dimensional shapes as opposed to two dimensional fabrics. The present invention can also be used to create custom designs using the spacer fabric that are customized to a user's needs.

The present invention may also be used for improved diabetic socks. Diabetics with vascular issues require extra protection especially in the foot. By controlling the areas of shock absorbing and impact protection, areas such as the sole, toes, and heel or any combination thereof can be better protected and provided with more comfort. Similarly, athletic socks would be improved by use of the present invention by controlling the cushioning and shock absorption areas for a specific high impact activity such as soccer, which places pressure on specific areas of the foot during an action, or even specified regions for a low impact activity like golf which results in different pressure on the foot. Finally, the present invention can be used for specialized standing socks to aid in the comfort of workers who stand for long durations such as construction workers and retail employees. Each of these applications would benefit from the machine-washable and breathable nature of the present invention.

Figure 32A:
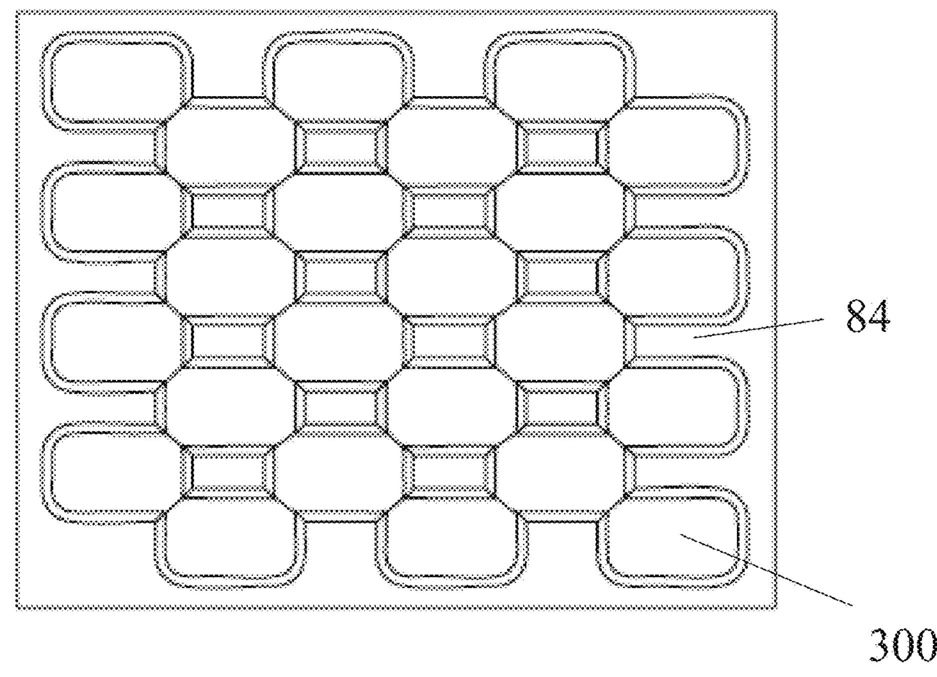
FIG. 32A-B is a perspective view of an alternative yarn with shock absorbing characteristics used in either the prosthetic liner version or sock version of the present invention.
Figure 32B:
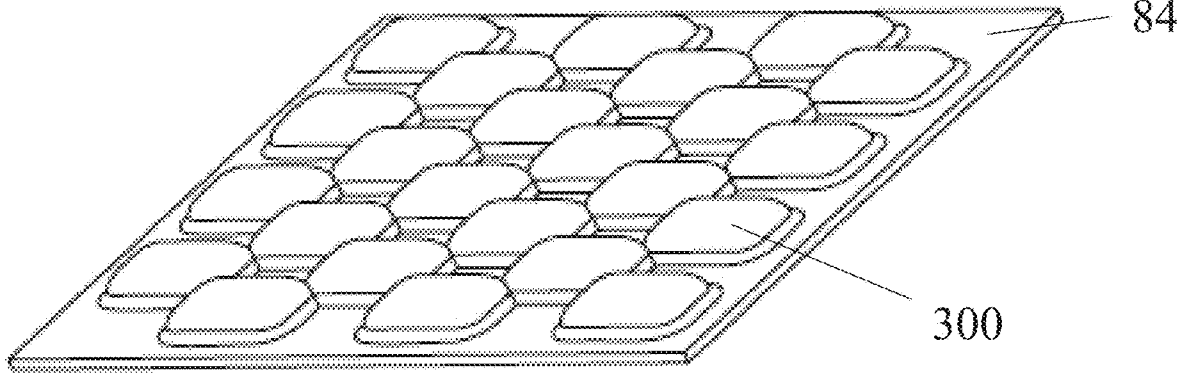

An alternative yarn that can be used preferably comprises a wool filament coated in poly(vinyl alcohol), also known as PVA. The PVA coating, once washed, allows for the inner wool fibers to expand thereby bulking the garment. Incorporating this alternative yarn with a traditional yarn using a tuck serves a dual purpose of keeping the alternative yarn in place and allowing for the creation of patterns caused by the alternative yarn expanding after washing which then can increase the shock absorbing characteristics of the sock/liner. For example, as seen in FIG. 32A-B, a checkerboard pattern or a striped pattern could be created. These expansion pockets 300 allow for comfort and warmth. The alternative yarn can also be wool, polypropylene, or other similar known or unknown natural or synthetic filaments that can be coated with PVA.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A shock absorbing prosthetic covering comprising:

a textile body comprising an open proximal end, a closed distal end, and sidewalls, wherein the closed distal end further comprises a distal region;

a spacer fabric comprising a multifilament natural fiber coated in a washable poly(vinyl alcohol) incorporated into a knittable filament thereby forming a plurality of expansion pockets;

wherein the shock absorbing prosthetic covering incorporates the spacer fabric into at least a portion of the distal region and the remainder of the shock absorbing prosthetic covering textile body comprises a thickness between 1 millimeter and 10 millimeters.

2. The shock absorbing prosthetic covering of claim 1 wherein the spacer fabric has a thickness between 4.5 millimeters and 9 millimeters.

3. The shock absorbing prosthetic covering of claim 1 wherein the multifilament natural fiber is wool.

4. A shock absorbing prosthetic covering comprising:

a textile body comprising an open proximal end, a closed distal end, and sidewalls, wherein the closed distal end further comprises a distal region;

a spacer fabric comprising multifilament synthetic fiber coated in a washable poly(vinyl alcohol) incorporated into a knittable filament thereby forming a plurality of expansion pockets;

wherein the shock absorbing prosthetic covering incorporates the spacer fabric into at least a portion of the distal region.

5. The shock absorbing prosthetic liner of claim 4 wherein the spacer fabric has a thickness between 4.5 millimeters and 9 millimeters.

6. The shock absorbing prosthetic covering of claim 4 wherein the textile body has a thickness between 1 millimeter and 10 millimeters.

7. The shock absorbing prosthetic liner of claim 4 wherein the multifilament synthetic fiber is polypropylene.

8. A shock absorbing prosthetic covering comprising:

a textile body comprising an open proximal end, a closed distal end, and sidewalls, wherein the closed distal end further comprises a distal region;

a spacer fabric comprising multifilament fiber coated in a washable poly(vinyl alcohol) incorporated into a knittable filament thereby forming a plurality of expansion pockets;

wherein the shock absorbing prosthetic covering incorporates the spacer fabric into at least a portion of the distal region.

9. The shock absorbing prosthetic covering of claim 8 wherein the spacer fabric has a thickness between 4.5 millimeters and 9 millimeters.

10. The shock absorbing prosthetic covering of claim 8 wherein the multifilament fiber comprises a wool filament and a polypropylene filament.

11. The shock absorbing prosthetic covering of claim 8 wherein the textile body has a thickness between 1 millimeter and 10 millimeters.

12. The shock absorbing prosthetic covering of claim 8 wherein the textile body further comprises a heel region.

13. The shock absorbing prosthetic covering of claim 12 wherein at least a portion of the heel region incorporates the spacer fabric.

* * * * *